(12) United States Patent
Hajianpour

(10) Patent No.: US 6,585,736 B2
(45) Date of Patent: Jul. 1, 2003

(54) DEVICE FOR EXTERNAL FIXATION OF A FRACTURED RADIUS WITH SIMULTANEOUS CLAMPING OF MULTIPLE PINS AND WITH A FIXTURE FOR APPLYING EXTENSION TO DISTAL BONE FRAGMENTS

(76) Inventor: Mohammed A. Hajianpour, 1706 Vestal Dr., Coral Springs, FL (US) 33065

( * ) Notice: Subject to any disclaimer, the term of this patent is extended or adjusted under 35 U.S.C. 154(b) by 67 days.

(21) Appl. No.: 09/956,314

(22) Filed: Sep. 19, 2001

(65) Prior Publication Data

US 2003/0055425 A1 Mar. 20, 2003

(51) Int. Cl.$^7$ ................................................ A61B 17/60
(52) U.S. Cl. .......................................... 606/57; 606/59
(58) Field of Search .............................. 606/54, 55, 56, 606/57, 58, 59, 60, 61, 67, 69, 70, 71, 72, 73

(56) References Cited

U.S. PATENT DOCUMENTS

| | | |
|---|---|---|
| 4,554,915 A | 11/1985 | Brumfield |
| 4,662,365 A | 5/1987 | Gotzen et al. |
| 4,714,076 A | 12/1987 | Conte et al. |
| 4,747,400 A | 5/1988 | Koeneman et al. |
| 4,867,144 A | 9/1989 | Karas et al. |
| 5,006,120 A | 4/1991 | Carter |
| 5,015,248 A | 5/1991 | Burstein et al. |
| 5,197,966 A | 3/1993 | Sommerkamp |
| 5,304,177 A * | 4/1994 | Pennig .......................... 606/58 |
| 5,545,162 A * | 8/1996 | Huebner ........................ 606/57 |
| 5,586,985 A * | 12/1996 | Putnam et al. ................ 606/69 |
| 5,741,251 A | 4/1998 | Benoist |
| 5,749,872 A | 5/1998 | Kyle et al. |
| 6,197,027 B1 * | 3/2001 | Hajianpour .................... 606/59 |

* cited by examiner

*Primary Examiner*—Pedro Philogene
(74) *Attorney, Agent, or Firm*—Ronald V. Davidge

(57) ABSTRACT

A fixture is configured to provide external fixation of a fractured distal radius by including a first number of holes for pins extending downward from the fixture into one or more bone fragments and a second number of holes for pins extending downward from the fixture into the shank of the radius. The fixture also includes a sliding block through which rods extend to hold pins directed laterally into the fragment(s). A sliding plate including a number of holes aligned with the first number of holes is moved by a pair of setscrews to clamp the pins extending through the first number of holes. The second number of holes includes a hole within a sliding structure allowing a single pin to be moved with a fixture to provide extension between the fragments and the shank of the radius.

22 Claims, 2 Drawing Sheets

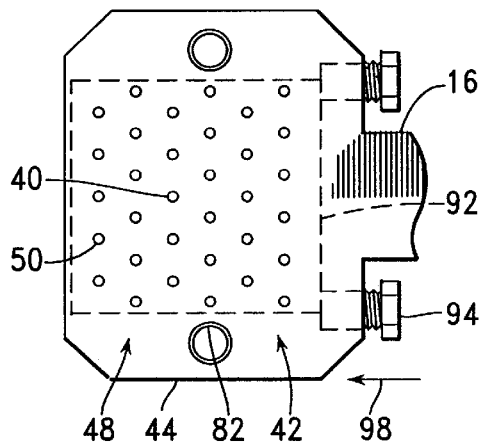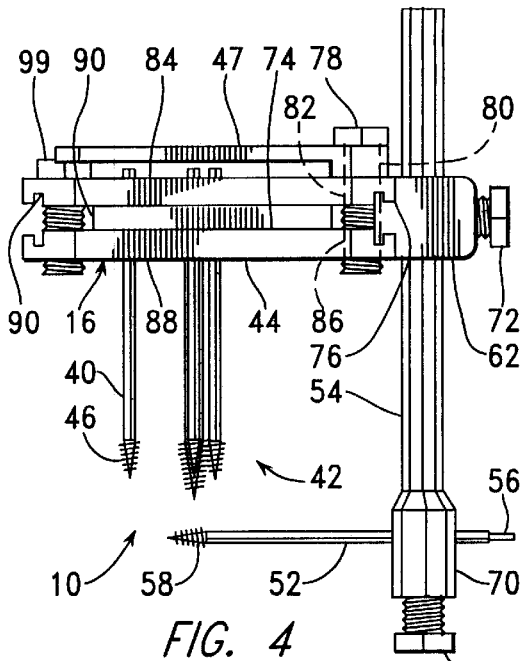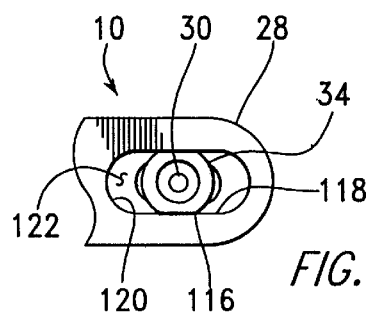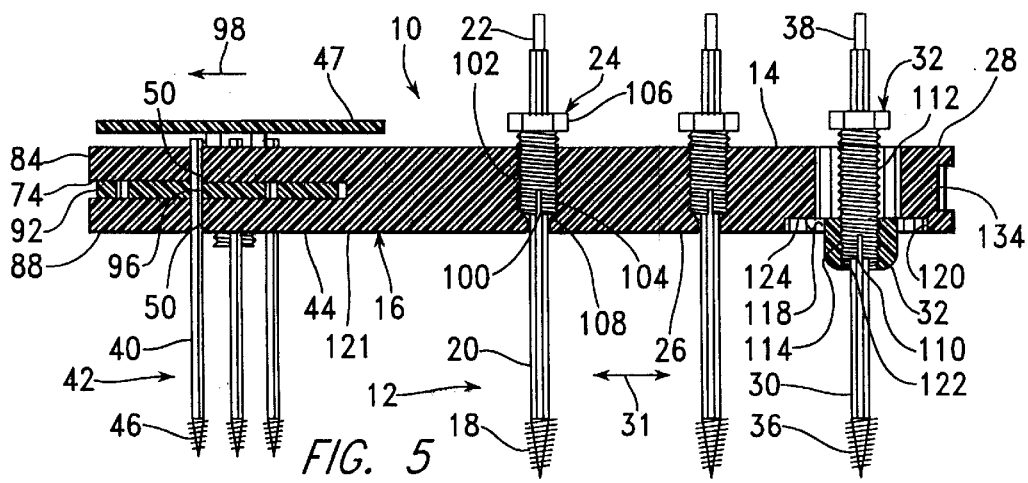

DEVICE FOR EXTERNAL FIXATION OF A FRACTURED RADIUS WITH SIMULTANEOUS CLAMPING OF MULTIPLE PINS AND WITH A FIXTURE FOR APPLYING EXTENSION TO DISTAL BONE FRAGMENTS

BACKGROUND OF THE INVENTION

1. Field of the Invention

This invention relates to clamping pins within devices for external fixation of fractured bones, and, more particularly, to an external fixture in which pins are clamped for fixation of a fractured radius.

2. Background Information

The fracture of the distal radius is one of the most common human fractures, occurring in as many as 350,000 people per year in the United States alone. The conventional processes both for reducing such a fracture and for maintaining the bones in proper alignment during the subsequent healing process involves applying and maintaining an extension force across the fracture, with ligamental taxis being relied upon to hold the bones in place. The process for treating a fractured distal radius is described in the 1901 edition of Gray's Anatomy in the following manner, "The treatment consists of flexing the forearm, and making a powerful extension from the wrist and elbow, depressing at the same time the radial side of the hand, and retaining the parts in that position by well-padded pistol-shaped splints."

A common method for the treatment of a fractured distal radius involves the use of standard immobilizing cast techniques, preventing movement of the radiocarpal joint throughout the course of rehabilitation. A problem with this method is that it sometimes results in inadequate internal fixation, which can cause deformity, pain, and prolonged disability.

The process of external pin fixation is often used in the repair of a fractured distal radius. This process initially involves the surgical insertion of skeletal traction pins on both sides of the fracture, with a frame being connected to the pins for immobilizing the bones, and for holding them together until the fracture is mended. Conventional methods for applying external pin fixation for the treatment of a fractured distal radius provide for the immobilization of the radiocarpal joint, so that the hand cannot be flexed.

While this type of fixation often provides an improvement over conventional casting techniques in the management of severe fractures of the distal radius, immobilization of the radiocarpal joint during the treatment period typically results in a long period of stiffness and disability after the external fixation device is removed. Typically, the external fixation device is left in place during the healing process for six to eight weeks. After the fixation device is removed, three to six months are required for the patient to regain motion of his hand.

An example of a fixation device providing adequate fixation during the healing process while allowing flexure in the radiocarpal joint is described in U.S. Pat. No. 6,197,027, the disclosure of which is incorporated herein by reference. This fixation device includes a number of pins clamped within pin mounting holes. Each pin extends through a flexible sleeve and through a clamping nut. Each pin-mounting hole includes a pilot hole guiding the pin and an internally threaded portion engaging an externally threaded portion of the clamping nut. As the clamping nut is tightened, the flexible sleeve is longitudinally compressed, so that it expands transversely to clamp itself within the pin-mounting hole and to clamp the pin within itself. The fixation device, which is configured particularly for external fixation of a fractured distal radius, includes a first number of such pins configured for attachment within a shaft portion of the radius and a second number of such pins configured to attachment to one or more fragments of the fractured radius. The fixation device also includes a sliding attachment block supporting a number of pins extending for lateral attachment to such a fragment.

However, in the holes used in the device of U.S. Pat. No. 6,197,027 to mount pins within the first number of pins, what is needed is a somewhat more simple, and therefore cost-effective, method for holding the pins in place. Such a method would preferably eliminate the need for the flexible sleeves to translate longitudinal compression into transverse clamping forces. In the holes used to mount pins within the second number of pins, what is needed is a more simple method, which will preferably clamp all of the pins in use simultaneously. Two or more of these pins may be used to clamp a single bone fragment in two or more places, or several pins may be used to clamp several bone fragments. Furthermore, since the process of setting a distal radius fracture typically includes an application of extension to the distal fragment(s), what is needed is a feature simplifying the application of such extension forces as the fixation device is installed on the fractured radius.

U.S. Pat. No. 5,545,162 describes a bone fixator including a proximal pin mounting block and a distal pin connected by a medial assembly, which connects the pin mounting blocks in a manner which is pivotally adjustable, and which further allows for adjustment of the distance between the pin mounting blocks. However, what is needed is a fixture for facilitating this distance adjustment so that it can be retained and gradually increased, instead of being lost when a clamping screw is loosened to allow movement. Furthermore, the method of U.S. Pat. No. 5,545,162 does not include the installation of pins within the fragments of bone; instead pins from the distal pin mounting block extend into the finger bones, adding a requirement that the extension forces must be directed through the wrist. To provide mobility of the hand and wrist, the fixture is pivoted with a ball joint. What is needed is a fixture rigidly holding pins extending into the bone fragments instead of into the bones of the fingers. Such a fixture would have advantages of holding different configurations of fragments in place, of holding them more rigidly, and of providing greater freedom of wrist movement.

SUMMARY OF THE INVENTION

Accordingly, it is a first objective of the present invention to provide a fixture and method for simultaneously clamping a number of pins extending into one or more fragments of a fractured bone.

It is another objective of the present invention to provide a convenient fixture and method for applying an extension to one or more fragments of bone relative to a remaining portion of bone.

According to a first aspect of the invention, a fixation device for holding a first number of pins extending into one or more fragments of a fractured bone and a second number of pins extending into another portion of the fractured bone, wherein the fixation device includes a main plate, a sliding plate, and a plate driving member. The main plate includes a first number of holes providing positions for the first plurality of pins and a second number of holes providing positions for clamping the second number of pins. The sliding plate is mounted to slide along the main plate. The sliding plate includes a third number of holes providing positions for the first number of pins as the first number of pins extend through the first plurality of holes. The plate driving member is movable in an engagement direction to slide the sliding plate along the first plate, simultaneously clamping pins extending through both the first and third pluralities of holes.

Preferably, the fixation device additionally includes a sliding pin holder slidably mounted on the main plate and releasably clamped in place on the main plate. A hole within the second number of holes extends within the sliding pin holder. Sliding the sliding pin holder in an extension-increasing direction increases a distance between a pin extending through the sliding pin holder and a pin extending through each hole in the first plurality of holes. Preferably, this fixation device also includes a frame removably attached to a pin extending through the sliding pin holder, and a setscrew moving the frame in the extension increasing direction.

According to another aspect of the invention, a method is provided for fixing one or more fragments of a fractured bone in place with respect to another portion of the fractured bone. The method includes:

a) surgically inserting a first plurality of pins, to extend through holes in a first plurality of holes within a main plate of a fixation device, into the one or more fragments of fractured bone;

b) clamping the first plurality of pins within holes in the first plurality of holes;

c) surgically inserting a sliding pin to extend through a hole within a sliding pin holder, mounted to slid along the main plate of the fixation device, into an other portion of the fractured bone;

d) after completing steps a) through c), sliding the sliding pin holder to establish extension between the one or more fragments of fractured bone and the other portion of fractured bone; and e) clamping the sliding pin holder in a location established in step c) to maintain the extension.

BRIEF DESCRIPTION OF THE FIGURES

FIG. 3 is a fragmentary plan view of the fixation device of FIG. 1, showing a distal end thereof;

FIG. 4 is a distal end view of the distal end of the fixation device of FIG. 1;

FIG. 5 is a longitudinal cross-sectional view of the fixation device of FIG. 1, taken as indicated by section lines V—V therein; and FIG. 6 is a fragmentary bottom plan view of the fixation device of FIG. 1, showing a proximal end thereof.

DETAILED DESCRIPTION OF THE INVENTION

Figure 1:
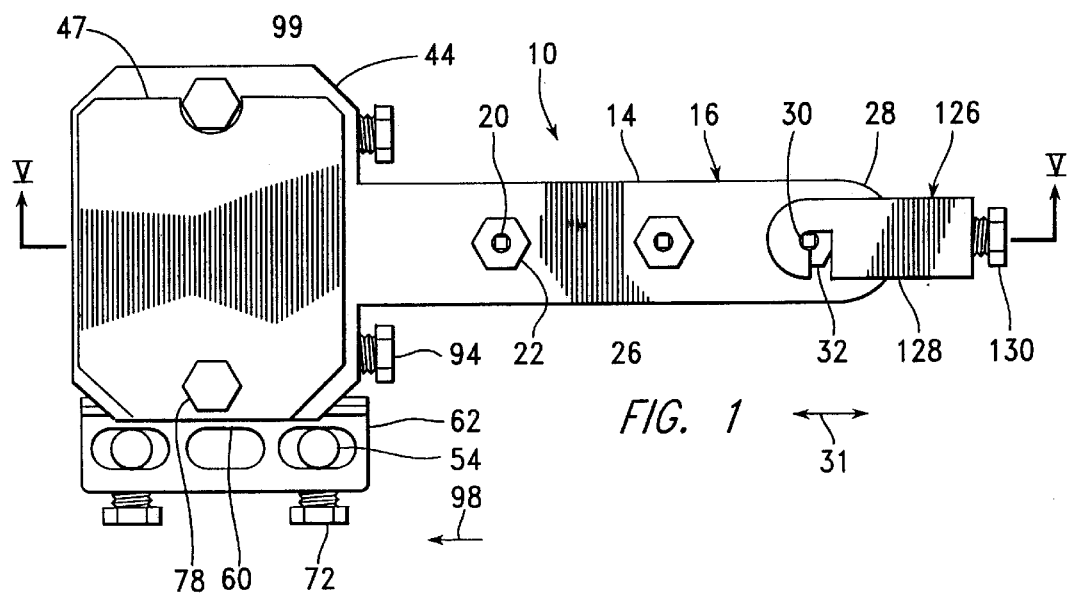
FIG. 1 is a plan view of a fixation device built in accordance with the present invention.

A fixation device 10, built in accordance with the present invention, will now be described, with initial reference be made to FIG. 1, a plan view of the device 10, and to FIG. 2, a front view thereof. The fixation device 10 is configured for surgical attachment to the shank portion of a radius bone (not shown) by means of a first pattern of pins 12, extending downward from an elongated section 14 of a plate 16, with the threaded end 18 of each pin 20 being screwed into the bone by means of a conventional driving device (not shown) engaging a non-circular coupling section 22 of each pin 20. The coupling section 22 is, for example, hexagonal or square. In the central portion 26 of the elongated section 14, a pair of clamping screws 24 is used to hold the pins 20 in a fixed relationship with the plate 16. Near the proximal end 28 of the elongated section 14, a slidable pin 30 is first mounted to slide in the longitudinal directions of arrow 31, and then, after tightening, to be held in place within the plate 16 by means of a clamping screw 32 and a nut 34. The slidable pin 30 is preferably identical to the pins 22, including a threaded portion 36 fastened into the bone shank and a non-circular coupling portion 38 for driving.

The fragment or fragments of the fractured distal radius Is/are held in place by means of a number of vertical fragment pins 40, within a second pattern of pins 42, extending downward from a widened distal portion 44 of the plate 16. Each of the pins 40 includes a threaded portion 46 for attachment within the bone fragment. In the example of FIGS. 1 and 2, the portions of pins 40 extending upward from the plate 16 are cut off after the pins 40 are fastened in place by means of non-circular coupling portions. While these coupling portions are not shown, they are understood to be similar to the coupling portions 22, 38 of the pins 20, 30, extending at the tips of the pins 40 before they are cut off. After the pins are cut off, their upward extending ends are covered with a cover plate 47.

FIG. 3 is a fragmentary plan view of the widened distal portion 44 of the plate 16, with the cover plate 47 removed to show a pattern 48 of holes 50, extending through the plate 16 for mounting the second pattern 42 of the vertical fragment pins 40.

FIG. 4 is a distal end view of the fixation device 10. One or more bone fragments can also be held in place with one, two, or three lateral fragment pins 52, extending inward from pin-mounting posts 54. These pins 52 are similar or identical to the vertical fragment pins 40, before the pins 40 are cut off, including a non-circular coupling portion 56 and threads 58 for attachment into bone.

Figure 2:
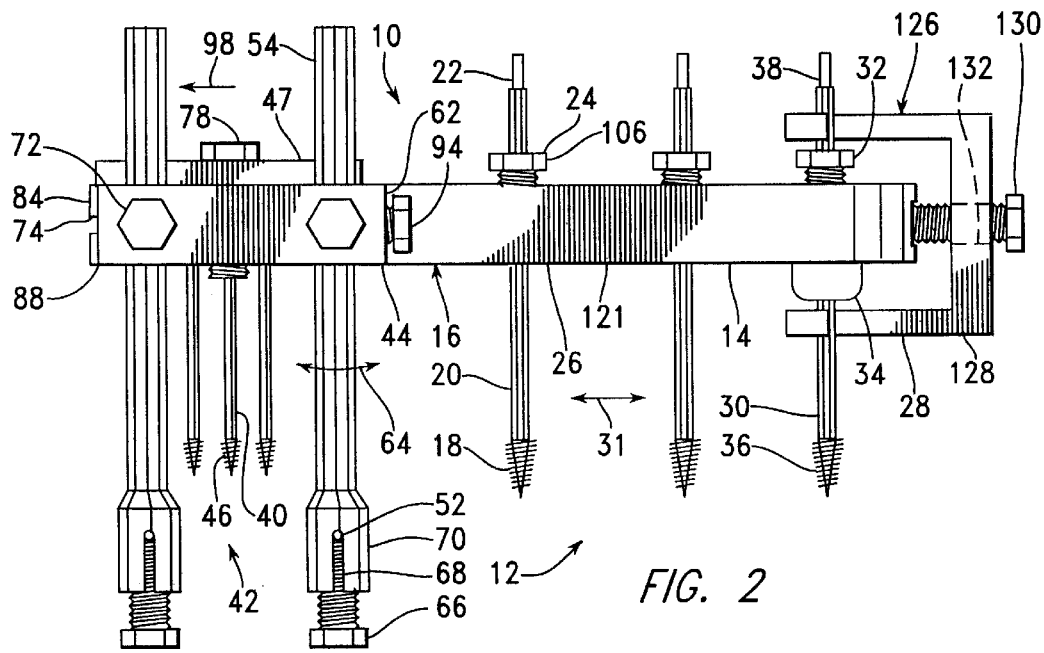
FIG. 2 is a front view of the fixation device of FIG. 1.

Referring to FIGS. 1, 2, and 4, each of the pin-mounting posts 54 is held within a slot 60 extending through a sliding block 62, which is mounted to slide in the longitudinal directions indicated by arrow 31. While two pin-mounting posts 54 are shown in the example of the figures, one, two, or three such posts 54 can be attached in this way. The elongation of the slots 60 provides for individual adjustment of the posts 54 in the longitudinal directions of arrow 31, and for adjustment of each post 54 in the angular directions of arrow 64. Each of the lateral fragment pins 52 is clamped, by means of a pin clamping screw 66, at the upper end of a slot 68 within an enlarged end 70 of the post 54. Each of the posts 54 is held in place within a slot 60 by means of a post clamping screw 72.

Referring additionally to FIG. 5, a longitudinal cross-sectional view of the fixation device 10, taken as indicated by section lines V—V in FIG. 1, the widened distal portion 44 of the plate 16 is bifurcated, being divided to include a slot 74. The sliding block 62 slides within a track 76 in the widened distal portion 44 of the plate 16, being clamped in place by a block clamping screw 78. The block clamping screw 78 extends through a clearance hole 80 in the cover plate 47 and a clearance hole 82 in the upper portion 84 of the widened distal portion 44, to engage a threaded hole 86 of the lower portion 88 of the widened distal portion 44.

The configuration shown in the figures is assembled particularly for treating a distal fracture of the right radius. For treating a distal fracture of the left radius, the lateral fragment pins 52 are arranged to extend inward from the opposite side of the fixation device 10 by mounting the sliding block 62 in an alternate track 90 within the widened distal portion 44.

The means used to clamp the pins 20, 30, 40 in place within the fixation device 10 will now be discussed, with initial reference being made to FIGS. 3 and 5. The fixation device 10 includes a pin-clamping plate 92, sliding within the slot 74, and a pair of plate-adjusting screws 94. The pin-clamping plate 92 includes a pattern of holes 96 aligned with the holes 50. Each of the holes 50 extends through both the upper portion 84 and the lower portion 88 of the widened distal portion 44. After the pins 40 to be used in a particular application of the fixation device 10 are inserted through the holes 50 and 96 with these holes 50 and 96 in alignment, the plate-adjusting screws 94 are used to drive the pin-clamping plate 92 in the direction of arrow 98, simultaneously clamping all of the pins 40. After the pins 40 are clamped in place in this way, both the block clamping screw 78 and a similar screw 99 on the opposite side of the widened distal portion 44 are tightened, clamping the pin-clamping plate in place within the slot 74. After the pins 40 are clamped in this way, the screws 78 and 99 are tightened to hold both the sliding block 62 and the sliding plate 92 rigidly in place.

Each pin-clamping screw 24 includes four slots 100, extending upward from the end of a threaded portion 102 of the screw 24 in a cruciform pattern to divide the lower part of this threaded portion 102 into four segments 104. As the screw 24 is driven downward by rotating its hexagonal head 106, the four lower segments 104 come into contact with a truncated conical surface 108 within the plate 16, forcing these segments 104 inward to clamp the pin 20 extending through the screw 24.

FIG. 6 is a fragmentary bottom plan view of the fixation device 10, particularly showing the proximal end 28 thereof. Referring to FIGS. 5 and 6, the pin-clamping screw 32, holding the sliding pin 30, While longer than the pin-clamping screws 24, is otherwise similar to these screws 24, including four slots 110 dividing the threaded section 112 into four lower segments 114. The nut 34 includes a pair of flat sides 116, which engage flat sides 118 of an elongated slot 120, extending along a lower surface 121 of the plate 16. The lower end of the internal threads 122 of the nut 34 is tapered inward. As the clamping screw 32 is rotated into increased engagement with the nut 34, the nut 34 moves upward into engagement with a surface 124 of the elongated slot 120, and the four lower segments 114 are driven inward to hold the sliding pin 30 in place.

According to a preferred version of the present invention, the fixation device 10 includes a removable extension-setting fixture 126, shown in FIGS. 1 and 2, which is configured to set a distance between the slidable pin 30 and other features of the fixation device 10. The extension-setting fixture 126 includes a frame 128 and a setscrew 130, which extends through a threaded hole 132 within the frame 128 to engage a proximal contact surface 134 (shown in FIG. 5) of the plate 16.

A preferred method for installing the fixation device 10 to provide both support and extension to a fractured radius will now be explained, with reference being made to FIGS. 1, 2, and 4. First, the sliding pin 30 is surgically inserted and driven into the shank portion of the radius, while the desired combination of fragment pins 40 and lateral fragment pins 52 are surgically implanted and driven into the distal fragment or fragments of the radius. The order in which these pins 30, 40, 52 are implanted and driven may be arbitrary, or may be determined by surgical considerations including the exact type of the fracture. The relationship between the sliding pin 30 and the other pins driven into the fragments must be such that the nut 32 holding the sliding pin 30 can subsequently be slid within the elongated slot 120 opposite the direction of arrow 98. Next, the setscrew 130 is tightened to move the pins 40 and 52 away from the sliding pin 30, providing a level of extension needed to properly set the fracture. Then, the pins 20 are surgically installed and driven into the radius. Finally, the setscrew 130 is loosened, and the extension-setting structure 126 is removed from the fixation device 10.

The pins 20, 30, 40, and 52 are preferably commercially available devices, which are conventionally composed of stainless steel. The frame 128 of the extension setting fixture 126 is preferably composed of aluminum. Other portions of the fixation device 10 are preferably composed of thermoplastic resins, with the screws being composed, for example, of nylon, and with the remaining parts being composed, for example, of polycarbonate. This use of thermoplastic materials makes it possible to form X-ray images of the bones through the fixation device 10. Furthermore, such materials provide a sufficient combination of strength and resiliency to allow a pattern of pins 40 to be clamped simultaneously as described above, in spite of dimensional variations between the patterns of holes holding the pins 40 in the sliding plate 92 and in the plate 16.

The fixation device 10 of the present invention has an advantage over the prior art fixation device of U.S. Pat. No. 5,545,162 in that, in the fixation device 10, the use of the extension-setting fixture 12 allows a distance of extension to be set gradually or incrementally, without loosing the set extension distance when a clamping screw is loosened. With the fixation device 10, the distance of extension may even be set as a number of turns of the screw 130. Also, the fixation device 10 has the advantage that at pins are inserted into the bone fragments, instead of into the finger bones, allowing rigid fixation of the fragments to the remaining portion of bone while maintaining flexibility of the hand and wrist.

While the present invention has been described in a preferred form or combination or embodiment with some degree of particularity, it is understood that this description has been given only by way of example, and that numerous changes in the details of fabrication and use, including the combination and rearrangement of parts, may be made without departing from the spirit and scope of the invention.

What is claimed is:

1. A fixation device for holding a first plurality of pins extending into one or more fragments of a fractured bone and a second plurality of pins extending into another portion of said fractured bone, wherein said fixation device comprises:

a main plate including a first plurality of holes providing positions for said first plurality of pins and a second plurality of holes providing positions for clamping said second plurality of pins;

a sliding plate mounted to slide along said main plate, wherein said sliding plate includes a third plurality of holes providing positions for said first plurality of pins as said first plurality of pins extend through said first plurality of holes; and a plate driving member movable in an engagement direction to slide said sliding plate along said first plate, simultaneously clamping pins extending through both said first and third pluralities of holes.

2. The fixation device of claim 1, wherein a portion of said main plate is bifurcated to form an upper section of said main plate, a lower section of said main plate, and a first slot extending between said upper and lower sections of said main plate, said sliding plate is mounted to slide between said upper and lower sections of said main plate, said first plurality of holes extend through said upper section of said main plate, and said main plate additionally includes a fourth plurality of holes providing positions for said first plurality of pins as said first plurality of pins extend through said first plurality of holes.

3. The fixation device of claim 1, wherein said plate driving member includes a first plate-adjusting screw sliding said sliding plate along said first plate.

4. The fixation device of claim 3, additionally comprising a second plate-adjusting screw sliding said sliding plate along said first plate.

5. The fixation device of claim 2, additionally comprising a plate-clamping screw clamping said sliding plate in position on said first plate.

6. The fixation device of claim 1, additionally comprising a sliding pin holder slidably mounted on said main plate and releasably clamped in place on said main plate, wherein a hole within said second plurality of holes extends within said sliding pin holder, and sliding said sliding pin holder in an extension increasing direction increases a distance between a pin extending through said sliding pin holder and a pin extending through each hole in said first plurality of holes.

7. The fixation device of claim 6, wherein said main plate includes an elongated hole, said sliding pin holder includes a nut sliding within said elongated hole and a sliding clamping screw with threads engaging said nut, and said hole extending within said sliding pin holder, extends through said sliding clamping screw.

8. The fixation device of claim 7, wherein said sliding clamping screw includes a number of flexible sections moving inward to engage said pin extending through said sliding pin holder as said sliding clamping screw is driven into engagement with said nut.

9. The fixation device of claim 8, additionally comprising:

a frame removably attached to a pin extending through said sliding pin holder, and a setscrew moving said frame in said extension increasing direction.

10. The fixation device of claim 1, additionally comprising a pin-clamping screw, wherein said frame includes an internally threaded hole, said pin-clamping screw extends within said internally threaded hole, said pin-clamping screw includes a number of flexible sections moving inward to engage said pin extending through said pin-clamping screw as said pin-clamping screw is driven into engagement with said internally threaded hole.

11. The fixation device of claim 1, additionally comprising an attachment block, slidably mounted on said first plate to move along and edge of said plate and to be clamped in place on said first plate, wherein said attachment block includes a plurality of rod mounting holes;

a rod, extending within a rod mounting hole within said plurality of rod mounting holes, and extending from said attachment block in a direction parallel to a pin extending though a hole within said first plurality of holes, wherein said rod includes a pin-mounting hole, extending perpendicular to said pin extending through a hole within said first plurality of holes and perpendicular to said rod.

12. A fixation device for holding a first plurality of pins extending into one or more fragments of a fractured bone and a second plurality of pins extending into another portion of said fractured bone, wherein said fixation device comprises:

a main plate including a first plurality of holes providing positions for said first plurality of pins and a second plurality of holes providing positions for clamping said second plurality of pins; and a sliding pin holder slidably mounted on said main plate and releasably clamped in place on said main plate, wherein a hole within said second plurality of holes extends within said sliding pin holder, and sliding said sliding pin holder in an extension increasing direction increases a distance between a pin extending through said sliding pin holder and a pin extending through each hole in said first plurality of holes.

13. The fixation device of claim 12, wherein said main plate includes an elongated hole, said sliding pin holder includes a nut sliding within said elongated hole and a sliding clamping screw with threads engaging said nut, and said hole extending within said sliding pin holder, extends through said sliding clamping screw.

14. The fixation device of claim 13, wherein said sliding clamping screw includes a number of flexible sections moving inward to engage said pin extending through said sliding pin holder as said sliding clamping screw is driven into engagement with said nut.

15. The fixation device of claim 12, additionally comprising:

a frame removably attached to a pin extending through said sliding pin holder, and a setscrew moving said frame in said extension increasing direction.

16. A method for fixing one or more fragments of a fractured bone in place with respect to an other portion of said fractured bone, wherein said method comprises:

a) surgically inserting a first plurality of pins, to extend through holes in a first plurality of holes within a main plate of a fixation device, into said one or more fragments of fractured bone;

b) clamping said first plurality of pins within holes in said first plurality of holes;

c) surgically inserting a sliding pin to extend through a hole within a sliding pin holder, mounted to slid along said main plate of said fixation device, into said other portion of said fractured bone;

d) after completing steps a) through c), sliding said sliding pin holder to establish extension between said one or more fragments of fractured bone and said other portion of fractured bone; and e) clamping said sliding pin holder in a location established in step c) to maintain said extension.

17. The method of claim 16, wherein
in step a), said first plurality of pins are additionally inserted to extend through holes in a second plurality of holes in a sliding plate mounted to slide on said main plate, and
step b) comprises sliding said sliding plate along said first plate and clamping said sliding plate in place to clamp said first plurality of pins within said fixation device.

18. The method of claim 16, wherein step d) includes
attaching a frame to said sliding pin; and
driving a setscrew to slide said frame with said sliding pin and said sliding pin holder.

19. The method of claim 18, additionally comprising removing said frame from said sliding pin.

20. The method of claim 16, wherein
step e) includes rotating a sliding pin clamping screw, engaging a nut mounted to slide within an elongated slot in said first plate, in an engagement direction,
rotating said sliding pin clamping screw in said engagement direction pulls said nut to move into engagement with a surface of said elongated slot, clamping said nut in place within said elongated slot, and
rotating said sliding pin clamping screw in said engagement direction drives flexible sections of said sliding pin clamping screw inward to clamp said sliding pin within a hole extending through said sliding pin clamping screw.

21. The method of claim 16, additionally comprising:
f) surgically inserting an additional pin to extend through a hole within a pin clamping holder engaging said first plate into said other portion of said bone, and
g) clamping said additional pin within said pin clamping holder.

22. The method of claim 16, wherein
said pin clamping holder includes an additional pin clamping screw, and
step h) includes rotating said pin clamping screw in an engagement direction to drive flexible sections of said additional pin clamping screw inward, clamping said additional pin within a hole extending through said additional pin clamping screw.

* * * * *